(12) United States Patent
Yoon et al.

(10) Patent No.: US 9,481,767 B2
(45) Date of Patent: Nov. 1, 2016

(54) POLY(4-HYDROXYBUTYRATE)-B-MONOMETHOXY(POLYETHYLENE GLYCOL) COPOLYMER NANOPARTICLES, PRODUCTION METHOD FOR SAME AND PHARMACEUTICAL COMPOSITION FOR BRAIN DISORDER TREATMENT CONTAINING SAME AS ACTIVE INGREDIENT

(71) Applicant: INDUSTRY-ACADEMIC COOPERATION FOUNDATION GYEONGSANG NATIONAL UNIVERSITY, Jinju-si (KR)

(72) Inventors: Sung-Chul Yoon, Jinju-si (KR); Mun-Hwan Choi, Jinju-si (KR); Mohsin Shah, Jinju-si (KR)

(73) Assignee: INDUSTRY-ACADEMIC COOPERATION FOUNDATION GYEONGSANG NATIONAL UNIVERSITY, Jinju-Si (KR)

( * ) Notice: Subject to any disclaimer, the term of this patent is extended or adjusted under 35 U.S.C. 154(b) by 31 days.

(21) Appl. No.: 14/624,262

(22) Filed: Feb. 17, 2015

(65) Prior Publication Data
US 2015/0158983 A1  Jun. 11, 2015

Related U.S. Application Data

(63) Continuation of application No. PCT/KR2013/007473, filed on Aug. 20, 2013.

(30) Foreign Application Priority Data

Aug. 21, 2012 (KR) .................. 10-2012-0091150

(51) Int. Cl.
| | |
|---|---|
| C08G 81/00 | (2006.01) |
| A61K 9/16 | (2006.01) |
| A61K 47/30 | (2006.01) |
| C08J 3/12 | (2006.01) |
| C08G 63/664 | (2006.01) |
| C08G 63/91 | (2006.01) |
| A61K 9/00 | (2006.01) |
| A61K 9/48 | (2006.01) |
| A61K 9/51 | (2006.01) |

(52) U.S. Cl.
CPC .............. *C08G 81/00* (2013.01); *A61K 9/0019* (2013.01); *A61K 9/4866* (2013.01); *A61K 9/5146* (2013.01); *C08G 63/664* (2013.01); *C08G 63/912* (2013.01)

(58) Field of Classification Search
None
See application file for complete search history.

(56) References Cited

FOREIGN PATENT DOCUMENTS

| KR | 2003-0011858 A | 2/2003 |
|---|---|---|
| KR | 2011-0096330 A | 8/2011 |

OTHER PUBLICATIONS

Shah, Poly(4-hydroxybutyrate)-b-monomethoxy (polyethylene glycol) Copolymer Nanoparticles as a Potential Drug Carriers, European Cells and Materials, vol. 20, Supplement 3, Aug. 24-27, 2010.*
Ravenelle, One-Step Synthesis of Amphiphilic Diblock Copolymers from Bacterial Poly([R]-3-hydroxybutyric acid), Biomacromolecules, 3, 1057-1064, Jul. 13, 2002.*
Martin, et al. Medical applications of poly-4-hydroxybutyrate: a strong flexible absorbable biomaterial, Biochemical Engineering Journal, 16, 97-105, Nov. 2003.*
van den Pol, Narcolepsy: A Neurodegenerative Disease of the Hypocretin System?, Neuron, 27, 415-418, Sep. 2000.*
Gref, et al. Biodegradable Long Circulating Polymeric Nanospheres, Science 263, 1600-1602, Mar. 18, 1994.*
Shah M et al., Poly(4-hydroxybutyrate)-b-monomethoxy (polyethyiene glycol) Copolymer Nanoparticles as a Potential Drug Carriers, European Cells and Materials. vol. 20, Suppl. 3 p. 236, 2010.
Shah M et al., Amorphous amphiphilic P(3HV-co-4HB)-b-mPEG block copolymer synthesized. European Journal of Pharmaceutics and Biopharmaceutics. vol. 80, pp. 518-527. 2012.
Shah M et al., Amphiphilic PHA-mPEG copolymeric nanocontainers for drug delivery. International Journal of Pharmaceutics. vol. 400, pp. 165-175. 2010.
International Search Report for PCT/KR2013/007473.

* cited by examiner

*Primary Examiner* — Randy Gulakowski
*Assistant Examiner* — Christopher M Rodd
(74) *Attorney, Agent, or Firm* — Joseph Hyosuk Kim; JHK Law

(57) ABSTRACT

The present invention relates to poly(4-hydroxybutyrate)-b-monomethoxy(polyethylene glycol) copolymer nanoparticles, a method for preparing the same, and a pharmaceutical composition including the same as an active ingredient for treating brain disorders, in which the P(4HB)-b-mPEG nanoparticles according to the present invention break down slowly in brain cells such that gamma-hydroxybutyric acid (GHB) is released and so can sustainedly release a therapeutic level of concentration of GHB which is used as an agent for treating brain disorders such as epilepsy, and the nanoparticles are in the form of a hydrophobic polymer and so cannot easily be used as a hallucinogenic agent or narcotic agent due to the hydrophobic property whereby said nanoparticles do not dissolve in water or alcohol, and so can be used more safely than existing GHB, and hence, can advantageously be used instead of prior-art GHB therapeutic agents.

6 Claims, 4 Drawing Sheets

POLY(4-HYDROXYBUTYRATE)-B-MONOMETHOXY(POLYETHYLENE GLYCOL) COPOLYMER NANOPARTICLES, PRODUCTION METHOD FOR SAME AND PHARMACEUTICAL COMPOSITION FOR BRAIN DISORDER TREATMENT CONTAINING SAME AS ACTIVE INGREDIENT

TECHNICAL FIELD

The present invention relates to poly(4-hydroxybutyrate)-b-monomethoxy(polyethylene glycol) copolymer nanoparticles, a method for preparing the same, and a pharmaceutical composition including the same as an active ingredient for treating brain disorders.

BACKGROUND ART

The stimulation of neural cells can be reduced by improving the inhibited synapse caused by gamma-aminobutyric acid (GABA), an inhibitory neurotransmitter of brain, and the anticonvulsant agents that inhibit GABA aminotransferase by which GABA is decomposed are expected to be used in developed countries in the near future. Particularly, a number of studies are conducted on γ-hydroxybutyric acid as a GABA neurotransmitter drug. GHB is a substance produced as a metabolite of γ-aminobutyric acid in brain, and because it functions as a neurotransmitter and a neuroregulator, the GHB has been clinically used as a therapeutic agent for cataplexy and narcolepsy, sedative, and treatment of alcoholism. In particular, the epileptic seizure that is completely blocked by the GHB in a mouse is known to be the best pharmacological model of viable antiepileptic drug for human use.

A γ-hydroxybutyric acid (4-hydroxybutanoic acid, C4H8O3), commonly abbreviated as GHB, is an endogenous substance, and a natural substance found in low amount in central nervous system, grapevine, beef, small citrus fruits and most other organisms. It is currently regulated in the United States, and marketed by Jazz Pharmaceuticals under the trade name, Xyrem.

However, γ-hydroxybutyric acid (GHB) is also an illegal chemical that is recognized as a major cause of drug related coma in the United States and other countries. As a matter of fact, the reported number of GHB overdose in the United States currently outweighs that of MDMA (ecstasy).

GHB, which also functions as a sedative of central nervous system (CNS) in a non-medical fashion is abused. Its various common names include liquid ecstasy and liquid X. GHB may induce the state of euphoria, hyperactivity and increase in enjoyment of music, increase in sexual desire, and increase in sociality at relatively low dose. At relatively high dose, GHB may induce nausea, dizziness, drowsiness, anxiety, visual disorder, hypoventilation, amnesia, unconsciousness, and death. The effect of GHB can persist 1.5 to 3 hours or longer if high dose is consumed or mixed with alcohol.

Some chemicals are converted into GHB in a stomach and during blood circulation. GBL or γ-butyrolactone is one of these prodrugs. Other prodrugs include 1,4-butanediol(1,4-B). The precursors thereof may include additional toxicity.

Although GHB was initially synthesized in France more than 40 years ago as an available anesthetic, it was rejected by medical institutes of the United States due to undesirable side effects. As more countries became aware of the above-described issue, the legalized use thereof is diminishing in most places. GHB is an orphan drug that was studied to treat complex disease of sleep disorders publicly known as hypnolepsy/cataplexy and was made public in 1987. At nearly the same time, the steroid users were informed that GHB may boost the production of growth hormone in body (in the state of deep sleep). However, due to the increased frequency of overdose, its marketing was interrupted in November, 1990. As a result of stricter regulation imposed on GHB, its homologues or related chemicals that can be converted to GHB in body have gained more popularity.

As conventional technologies to replace the above-described GHB, the chemicals containing the first residue that is covalently bonded to the second residue through amino terminal or acidic terminal other than a carboxylic acid group and the second residue, in which the first residue is an analogue or a derivative of γ-aminobutyric acid (GABA) or GABA, is described in International Application No. WO 2010/042759 and in Korean Patent No. 957772, the high 4HB producing mutant to which the genes encoding enzymes that convert succinate to 4HB (4-hydroxybutyrate) are introduced and lacking the genes encoding enzymes that convert succinate semialdehyde to succinate and the preparation method of 4HB using the mutant are described.

However, the development of a therapeutic agent that can substitute GHB, can be safely administered due to alcohol insolubility, and has the similar treatment effect to that of GHB is still required.

DISCLOSURE

Technical Problem

An object of the present invention is directed to providing a pharmaceutical composition capable of substituting GHB, being administered safely due to alcohol insolubility, and exhibiting treatment effect similar to that of GHB.

Technical Solution

In order to achieve the above-described object, the present invention provides poly(4-hydroxybutyrate)-b-monomethoxy(polyethylene glycol) copolymer nanoparticles (hereafter, P(4HB)-b-mPEG), in which the surfaces thereof are composed of polyethylene glycol and the cores thereof are composed of polyhydroxyalkanoic acid (PHA).

Moreover, the present invention provides a method for preparing P(4HB)-b-mPEG nanoparticles, in which the method includes:

a step of preparing poly(4-hydroxybutyrate) (hereafter, P(4HB)) (Step 1);

a step of coupling monomethoxy(polyethylene glycol) (hereafter, mPEG) to the terminus of the above-described P(4HB) (Step 2); and a step of preparing nanoparticles using a self-assembly method (Step 3).

Furthermore, the present invention provides a pharmaceutical composition including the above-described P(4HB)-b-mPEG as an active ingredient for treating brain disorders.

Advantageous Effects

The P(4HB)-b-mPEG nanoparticles according to the present invention can continuously release GHB, which is used as a therapeutic agent for brain disorders such as epilepsy, in a therapeutic concentration, because they are decomposed slowly in brain cells, and then, releases a γ-hydroxybutyric acid (GHB). In addition, the P(4HB)-b-mPEG nanoparticles can substitute the previously used GHB therapeutic agents and can be advantageously used because they can be used more safely than the existing GHB, due to the fact that the nanoparticles are in the form of hydrophobic polymer, which makes them unable to be used either as a hallucinogenic agent or as a narcotic agent because of the hydrophobic property whereby they are insoluble in water or alcohol.

MODES OF THE INVENTION

Hereinafter, the present invention will be described in detail.

The present invention provides poly(4-hydroxybutyrate)-b-monomethoxy(polyethylene glycol) copolymer nanoparticles (hereafter, P(4HB)-b-mPEG), in which the surfaces thereof are composed of polyethylene glycol and the cores thereof are composed of polyhydroxyalkanoic acid (PHA).

Figure 1:
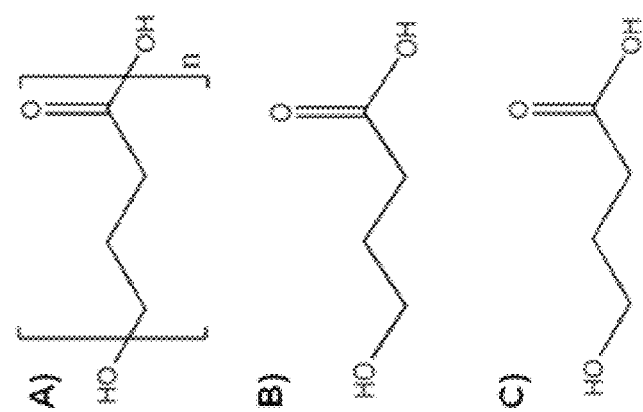
FIGS. 1A-1C show a diagram illustrating the similarity of GHB and the monomeric units prepared by decomposing the P(4HB) according to the present invention with depolymerase.
Figure 2:
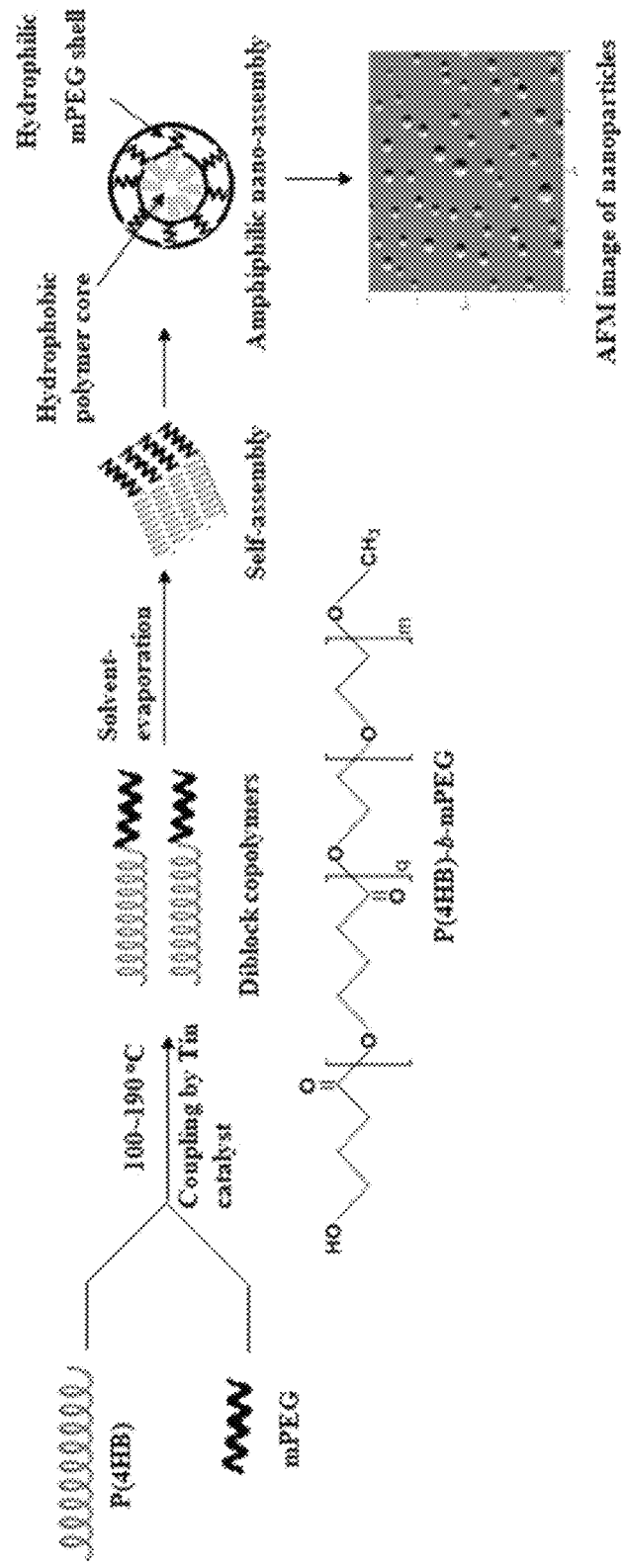
FIG. 2 is a schematic diagram illustrating the structure of the P(4HB)-b-mPEG nanoparticles according to the present invention and the self-assembly process thereof.

To be more specific, as illustrated in FIG. 2, the P(4HB)-b-mPEG nanoparticles according to the present invention has the structure, in which the cores of nanoparticles are composed of the polyhydroxyalknoic acids, such as poly(4-hydroxybutyrate), and polyethylene glycol is bound to the surface of the nanoparticles. The nanoparticles according to the present invention cannot easily be used as a hallucinogenic agent or a narcotic agent, because a hydrophobic property is generated due to the polymer form of polyethylene glycols on the surface of the nanoparticles, and thus, the nanoparticles are insoluble in water or alcohol. In addition, as illustrated in FIG. 1, since the poly(4-hydroxybutyrate) in the cores of the nanoparticles is decomposed into γ-hydroxybutyric acid (GHB) by depolymerase or partial hydrolysis, and thus, released, the poly(4-hydroxybutyrate) can be constantly used to treat brain disorders, such as, an epilepsy.

Furthermore, the present invention provides a method for preparing P(4HB)-b-mPEG nanoparticles, in which the method includes:

a step of preparing poly(4-hydroxybutyrate) (hereafter, P(4HB)) (Step 1);

a step of coupling monomethoxy(polyethylene glycol) (hereafter, mPEG) to the terminus of the P(4HB) (Step 2); and a step of preparing nanoparticles using a self-assembly method (Step 3).

First, Step 1 is a step of preparing P(4HB).

The P(4HB) may be prepared using the known methods in the related art, and for example, may be prepared using an organic synthesis or specific bacteria, but the present invention is not limited thereto.

When the organic synthesis is used, the P(4HB) may be prepared by performing a transesterification reaction under the presence of a bis(2-ethylhexanoate) tin catalyst, and when the bacteria are used, *Hydrogenophaga pseudoflava*, recombinant *Escherichia coli* K12, and the like may be used as the bacteria. The P(4HB) accumulated in the bacteria may be used in the next steps after being extracted from the dried cells using chloroform and being separated by a methanol reprecipitation.

Next, Step 2 is a step of coupling mPEG to the terminus of the P(4HB).

As a coupling method of the mPEG, the known methods in the related art may be used, and for example, an esterification reaction method using a tin-alkanoate catalyst may be used, and more specifically, a melt-esterification reaction method without using a solvent may be used, which is performed in a nitrogenous environment at the reaction temperature of 100 to 190° C. for the reaction time of 20 to 50 minutes.

Next, Step 3 is a step of preparing nanoparticles using a self-assembly method.

The self-assembly method may be conducted by dissolving the coupled P(4HB)-b-mPEG block polymer in chloroform, and then, dispersing the coupled P(4HB)-b-mPEG block polymer dissolved in chloroform in water (namely, dispersing slowly the polymer at room temperature, removing a standing solvent in an overnight hood, and then, freeze-drying), but the present invention is not limited thereto.

Figure 3:
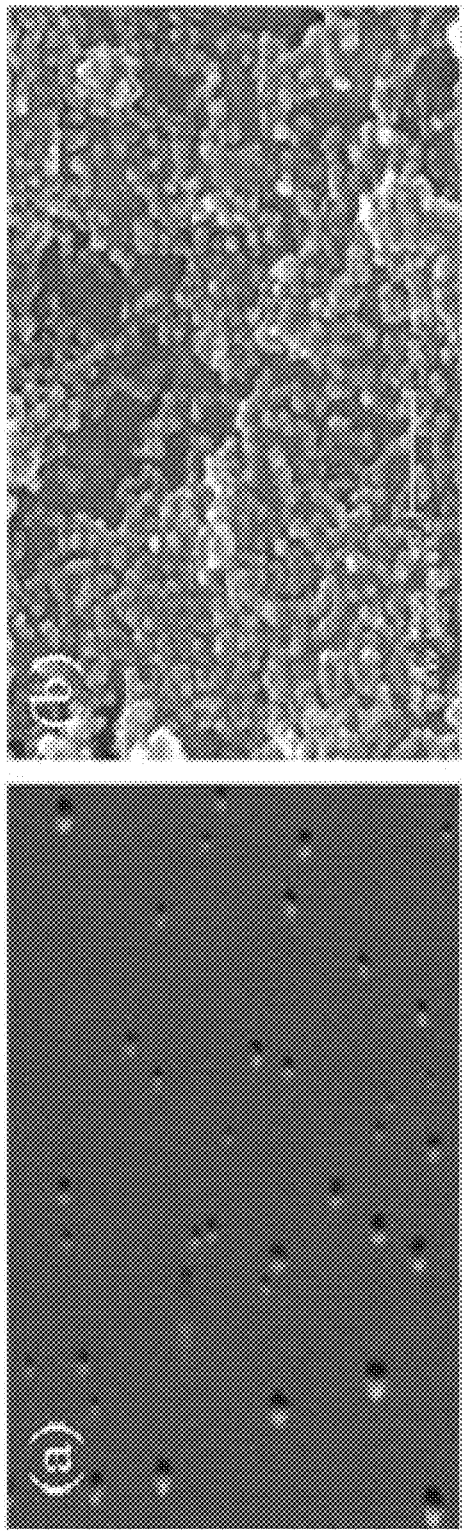
FIGS. 3A-3B show a diagram illustrating the morphology of the P(4HB)-b-mPEG nanoparticles according to the present invention ((a) AFM image, (b) FE-SEM micrograph).

It is known that the nanoparticles with a diameter of 20 to 100 nm are prepared by the above-described method (see FIG. 3).

Furthermore, the present invention provides a pharmaceutical composition including the P(4HB)-b-mPEG nanoparticle as an active ingredient for treating brain disorders.

Figure 4:
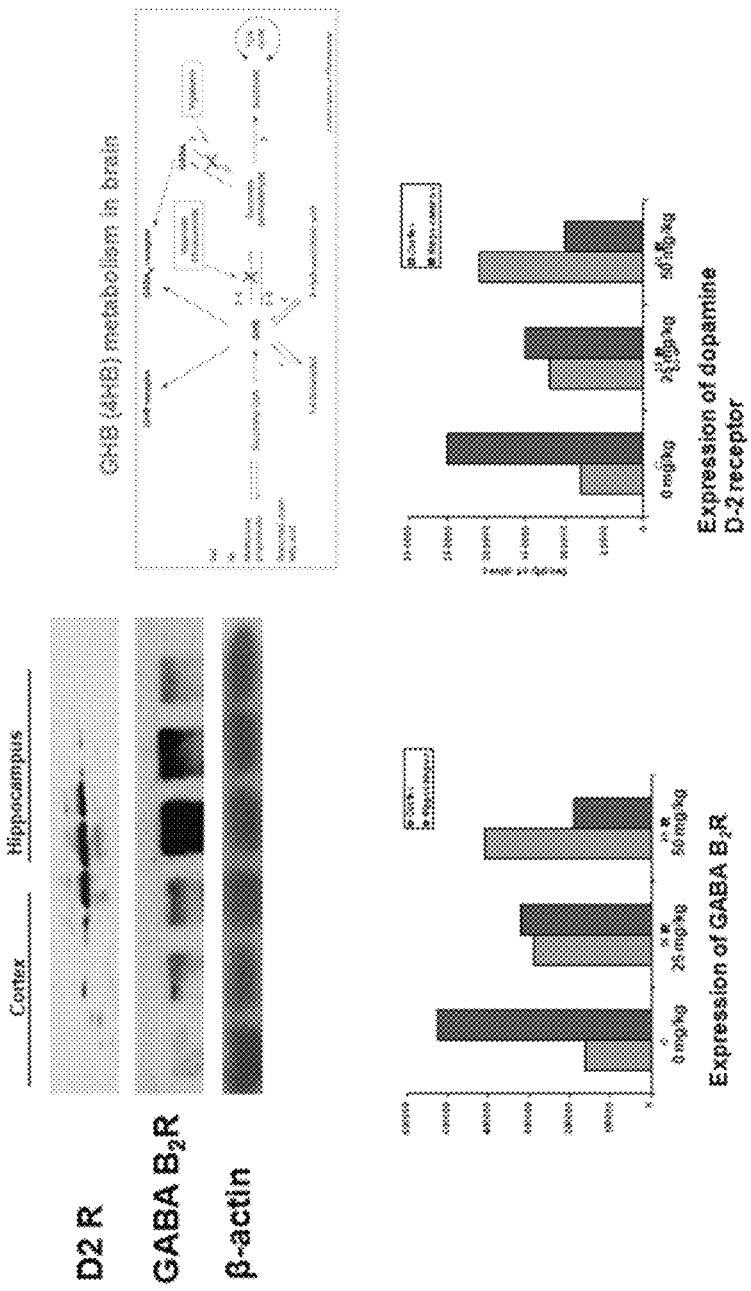
FIG. 4 is a graph illustrating an epilepsy treatment effect of the P(4HB)-b-mPEG nanoparticles according to the present invention, in which the P(4HB)-b-mPEG nanoparticles are slowly decomposed in brain, and subsequently, exhibits the effect of GHB by passing the P(4HB)-b-mPEG nanoparticles through the blood brain barrier (BBB) of the brain, and thus, affecting the expression of a GHB-related protein.

The P(4HB)-b-mPEG nanoparticles is exhibited in the amount of less than 50 mg/kg in an experiment on epilepsy-related brain disorders, and thus, exhibits an epileptic effect (see FIG. 4). Moreover, using a rat (about 250 g ea), ½ ml of the P(4HB)-b-mPEG nanoparticle dispersion (phosphate buffer is used as carrier) is intraperitoneally administered to the rat once a day for 14 days, and 2 weeks later, the expression of GHB-related protein is observed using a cortex and hippocampus specimen. As a result, it can be confirmed that there are effects of treating and improving the symptoms of brain disorders including epilepsy.

Therefore, a pharmaceutical composition including the P(4HB)-b-mPEG nanoparticles according to the present invention as an active ingredient may advantageously be used for treating brain disorders such as epilepsy.

When being clinically administered, the nanoparticles according to the present invention may be administered in various formulations, such as, an oral and parenteral formulations, and when being formulated, it is prepared using diluents or excipients, such as, fillers, extending agents, bonding agents, wetting agents, disintegrating agents, and surfactants, which are commonly used.

A solid formulation for an oral administration includes tablets, pills, powders, granules, capsules and troches, and these solid formulations are prepared by adding at least one excipient, for example, starch, calcium carbonate, sucrose, lactose, or gelatin to the compound of the present invention.

Additionally, in addition to simple excipient, lubricants, such as magnesium stearate talc are also used. As a liquid formulation for an oral administration, there are suspension, oral solution, emulsion and syrup, and in addition to water and liquid paraffin that are commonly used simple diluents, various excipients, for example, wetting agents, sweeteners, aromatics, and preservatives may be included.

As a formulation for a parenteral administration, sterilized aqueous solutions, non-aqueous solvents, suspensions, emulsions, lyophilized preparations, and suppositories are included. As the non-aqueous solvents and suspensions, vegetable oil, such as, propylene glycol, polyethylene glycol, and olive oil, and injectable ester, such as, ethyl oleate may be used. As a base of suppository, Witepsol, macrogol, Tween 61, cacao butter, laurinum, and glycerol, gelatin, and the like may be used.

Furthermore, the effective dose of the nanoparticles of the present invention to a human body varies depending on the age, weight, and gender of a patient, a route of administration to a patient, a health condition of a patient, and the severity of disease of a patient, but generally, the effective dose is about 0.001 to 100 mg/kg/day, and preferably 0.01 to 50 mg/kg/day. With respect to a 70 kg adult patient, the effective dose is generally 0.07 to 7000 mg/day, and preferably, 0.7 to 2500 mg/day, and depending on the assessment made by physicians or pharmacists, the effective dose may be administered with a defined time interval once a day or several times a day.

Hereinafter, the present invention will be described in detail with reference to Examples. However, the following Examples are only for illustrating the present invention, and the content of the present invention is not limited to the following Examples.

Examples

Production of P(4HB)-b-mPEG Nanoparticles

The P(4HB)-b-mPEG copolymer was prepared by performing a transesterification reaction under the presence of a bis(ethylhexanoate) tin catalyst according to the literature [F. Ravenelle, and R. H. Marchessault (2002) Biomacromolecules 3:1057-1064]. The structure of the product was determined by GPC, $^1$H-NMR, and DSC analysis. From the diblock copolymer, the nanoparticles were prepared using emulsification-solvent evaporation technique, as described previously (Budhian et al., 2007). The morphology of the nanoparticles was determined by AFM and FE-SEM. In order to identify the surface charge and mean diameter of the nanoparticles, DLS and ELS were used.

The surface morphology of prepared nanoparticles was measured, and then, the results are illustrated in FIG. 3.

As illustrated in FIG. 3, for the particles prepared, it can be confirmed that the nanoparticles have the diameter of 100 nm or less.

Experimental Example

Effect of Epilepsy Treatment

In order to investigate the effect of the nanoparticles according to the present invention on treating epilepsy, the following experiments were conducted.

Using male adult rats weighing 250 g each (the experiments were conducted under three different concentration, 0, 25, and 50 mg/kg of body weight), ½ ml of P(4HB)-b-mPEG nanoparticle dispersion (a phosphate buffer was used as carrier) was intraperitoneally administered to the rats once a day for 14 days. 2 weeks later, the expressions of relevant proteins exhibiting the responses to the administration of GHB were observed by a western blotting using a cortex and hippocampus specimen.

As a result, it can be confirmed that the nanoparticles according to the present invention have the effects on improving and treating the symptoms of epilepsy.

Hereinafter, Formulation Examples for the composition of the present invention will be described.

Formulation Examples

Preparation of Pharmaceutical Formulation

<1-1> Preparation of Powder
2 g of P(4HB)-b-mPEG nanoparticles
1 g of lactose

The above-described ingredients were mixed, and then, the mixed ingredients were filled in an airtight bag to prepare a powder.

<1-2> Preparation of Tablet
100 mg of P(4HB)-b-mPEG nanoparticles
100 mg of corn starch
100 mg of lactose
2 mg of stearic acid magnesium The above-described ingredients were mixed, and then, the mixed ingredients were subjected to a tableting process according to a general method of preparing a tablet to prepare a tablet.

<1-3> Preparation of Capsule
100 mg of P(4HB)-b-mPEG nanoparticles
100 mg of corn starch
100 mg of lactose
2 mg of stearic acid magnesium The above-described ingredients were mixed, and then, the mixed ingredients were filled in a gelatin capsule according to a general method of preparing a capsule to prepare a capsule.

<1-4> Preparation of Injection Solution
10 μg/ml of P(4HB)-b-mPEG nanoparticles
Adjust pH to 3.5 using diluted hydrochloric acid BP The imidazole derivatives according to the present invention were dissolved in an appropriate volume of sodium chloride BP for injection, the pH of the produced solution was adjusted to pH 3.5 by using diluted hydrochloric acid BP, and then the volume thereof was adjusted with sodium chloride BP for injection and mixed thoroughly. The solution was filled in a 5 ml-type I ampoule made of a transparent glass, and the glass was dissolved, thereby sealing the ampoule under the upper lattice of air, and subsequently, the ampoule was subjected to UV sterilization for 10 minutes or more at room temperature.

The project identification numbers of the national R & D project from which supports were provided for the present invention are 2009-0070747 and 2012-0009522, funded by National Research Foundation of Korea, Ministry of Science, ICT and Future Planning, which was supervised by Gyeongsang National University.

Hitherto, the present invention was addressed mainly by the favorable exemplary embodiments thereof. An ordinary skill in the art to which the present invention belongs will understand that the present invention can be transformed and implemented without deviating from the essential properties thereof. Thus, all exemplary embodiments disclosed herein should be considered not in terms of limited aspects, but in terms of descriptive aspects. The scope of the present invention is not shown in the aforementioned description, but in the scope of request for a patent and all discrepancies existing in the equivalent scope should be regarded as included in the present invention.

The invention claimed is:

1. A method for treating epilepsy, comprising administering to a subject in need thereof as an active ingredient, poly(4-hydroxybutyrate)-b-monomethoxy(polyethylene glycol) copolymer nanoparticle (hereinafter, P(4HB)-b-mPEG nanoparticle), wherein surface of the nanoparticle is composed of polyethylene glycol and core of the nanoparticle is composed of polyhydroxybutyrate.

2. The method for treating according to claim 1, wherein the administering is by parenteral or oral administration.

3. The method for treating according to claim 1, wherein the P(4HB)-b-mPEG nanoparticle is prepared comprising the steps of:

a step of preparing poly(4-hydroxybutyrate) (hereafter, P(4HB)) (Step 1);

a step of coupling monomethoxy(polyethylene glycol) (hereafter, mPEG) to a terminus of the P(4HB) (Step 2); and a step of preparing nanoparticles using a self-assembly method (Step 3).

4. The method for treating according to claim 3, wherein the poly(4-hydroxybutyrate) in the Step 1 is prepared by an organic synthesis or bacteria.

5. The method for treating according to claim 3, wherein the Step 2 is performed by a melt-esterification reaction without using a solvent under a nitrogenous environment using a tin-alkanoate catalyst at a reaction temperature of 100 to 190° C. for a reaction time of 20 to 50 minutes.

6. The method for treating according to claim 3, wherein the Step 3 is performed by a water dispersion method and a solvent evaporation method.

* * * * *